(12) United States Patent
Karmaker et al.

(10) Patent No.: US 7,673,550 B2
(45) Date of Patent: Mar. 9, 2010

(54) FIBER-REINFORCED COMPOSITES FOR DENTAL MATERIALS

(75) Inventors: Ajit Karmaker, Wallingford, CT (US); Arun Prasad, Cheshire, CT (US)

(73) Assignee: Pentron Clincal Technologies, LLC, Wallingford, CT (US)

( * ) Notice: Subject to any disclaimer, the term of this patent is extended or adjusted under 35 U.S.C. 154(b) by 1011 days.

(21) Appl. No.: 11/385,595

(22) Filed: Mar. 21, 2006

(65) Prior Publication Data
US 2006/0208393 A1 Sep. 21, 2006

(51) Int. Cl.
*D04C 1/02* (2006.01)

(52) U.S. Cl. .................................. 87/1; 87/6

(58) Field of Classification Search ............ 87/1, 87/6, 9, 13; 427/2.29; D24/156, 176; 428/365, 428/375, 377
See application file for complete search history.

(56) References Cited

U.S. PATENT DOCUMENTS

| | | | |
|---|---|---|---|
| 3,066,112 A | 11/1962 | Bowen | |
| 3,179,784 A | 4/1965 | Johnson | |
| 3,194,784 A | 7/1965 | Bowen | |
| 3,751,399 A | 8/1973 | Lee et al. | |
| 3,926,906 A | 12/1975 | Lee, II et al. | |
| 3,960,050 A * | 6/1976 | Eisler ........................... | 87/1 |
| 4,544,359 A | 10/1985 | Wakine | |
| 4,547,531 A | 10/1985 | Wakine | |
| 4,717,341 A | 1/1988 | Goldberg et al. | |
| 4,894,012 A | 1/1990 | Goldberg et al. | |
| 4,902,297 A * | 2/1990 | Devanathan ............. | 623/23.51 |
| 5,276,068 A | 1/1994 | Wakine | |
| 5,564,929 A | 10/1996 | Alpert | |
| 5,846,640 A | 12/1998 | Vallittu | |
| 5,919,044 A | 7/1999 | Sicurelli, Jr. et al. | |
| 5,921,778 A | 7/1999 | Karmaker et al. | |
| 5,934,168 A * | 8/1999 | Feichtinger et al. ............. | 87/8 |
| 6,030,220 A | 2/2000 | Karmaker et al. | |
| 6,039,569 A | 3/2000 | Prasad et al. | |
| 6,114,409 A | 9/2000 | Krebber | |
| 6,197,410 B1 | 3/2001 | Vallittu et al. | |
| 6,381,989 B1 | 5/2002 | Karmaker et al. | |
| 6,595,776 B2 | 7/2003 | Kangasniemi et al. | |
| 6,733,288 B2 | 5/2004 | Vallittu et al. | |
| 2003/0068598 A1 | 4/2003 | Vallittu et al. | |

\* cited by examiner

FOREIGN PATENT DOCUMENTS

| | | |
|---|---|---|
| WO | WO 01/50979 A1 | 7/2001 |
| WO | WO 02/100355 A1 | 12/2002 |
| WO | WO 03/105785 A1 | 12/2003 |

*Primary Examiner*—Shaun R Hurley
(74) *Attorney, Agent, or Firm*—Wood, Herron & Evans, LLP

(57) ABSTRACT

A formable fiber-reinforced composite having an inner core of fiber-reinforced composite surrounded by a sheath of fiber-reinforced composite material. The inner core of fiber-reinforced composite has a plurality of longitudinally extending fibers disposed in a resin matrix material and formed in the shape of a rod. The sheath has woven or braided fibers impregnated with a resin matrix material in the form of a sleeve. A method of manufacturing the formable fiber-reinforced composite material is provided. The longitudinally extending fibers in resin matrix material is cured to provide a solid rod. A sheath is placed around the rod. The rod with sheath is treated (e.g., heat, chemical solution, or both) to remove the resin matrix material. Thereafter, the rod and sheath are impregnated with a resin matrix material. The resin is left uncured or partially cured to provide a formable fiber-reinforced composite material. The formable material may be flattened.

34 Claims, 1 Drawing Sheet

FIBER-REINFORCED COMPOSITES FOR DENTAL MATERIALS

FIELD OF THE INVENTION

This invention relates to resin impregnated composites having manageable formability and handling characteristics for use in dental applications such as crowns, bridges, frameworks, clasps, inlays, onlays, fillings, splints, partial and full dentures, implants, posts, cores, and orthodontic materials.

BACKGROUND OF THE INVENTION

Current fiber composites have either good mechanical properties with less formable consistency or good formability with poor mechanical properties. In cases where the impregnated composites need to be pushed between teeth or formed therein, the fibers tend to fray resulting in difficult manipulation. The fraying of the fibers also occurs when the strips are cut into small pieces. One cause of the problem is the high elastic memory of the reinforcing fibers, which are frequently fabricated of fiberglass.

The fraying may be minimized by using heat treated woven tape made of fiberglass as set forth in U.S. Pat. No. 6,381,989 B1 to Karmaker et al., which is hereby incorporated by reference. However, the woven structure does not provide adequate mechanical properties as continuous fiber would and, therefore, is not suitable for many applications where higher strength is required such as in dental bridges.

Another approach involves embedding woven cloths of organic/inorganic fibers as disclosed in U.S. Pat. No. 6,114,409 to Krebber, which is hereby incorporated by reference. Products based on U.S. Pat. No. 6,114,409 include cloths of organic fibers such as polyethylene and polyester, embedded into highly filled dental composites. Some of the drawbacks of these products may be: a) the organic fibers do not provide satisfactory adhesion to the dental resin and therefore are prone to delamination; b) three-point bend test results have shown that products made of polyethylene and polyester embedded into highly filled dental composites have an average flexural strength of about $72\pm19$ MPa that is even lower than many particulate filled composites; c) the fiber content is low in order to keep good formability, thus any reinforcing effect is also very minor; d) if inorganic fibers such as fiberglass are used, the amount of filled resin content has to be much higher in order to suppress the high elastic memory of such fibers and consequently will not provide adequate strength.

In another attempt, U.S. Pat. No. 6,197,410, hereby incorporated by reference, discloses reinforced composite resins having improved handling characteristics by using poly methyl methacrylate (PMMA) in the matrix resin. Products made under this patent have PMMA in the matrix and also in a sheath surrounding the fiber bundle. Consequently, the surface is dry and does not adhere well when layering multiple strips during the fabrication of dental restorations. Alternatively, it is recommended that the strip surface be pre-wetted with liquid material, which results in a weak interphase between multiple strips producing a potentially weak restoration.

It would be desirable to provide a dental material fabricated of resin-impregnated composites and having good formability and handling. It would beneficial that the dental material also exhibit adequate mechanical properties.

SUMMARY OF THE INVENTION

These and other objects and advantages are accomplished by a formable fiber-reinforced composite having an inner core of fiber-reinforced composite surrounded by a sheath of fiber-reinforced composite material. The inner core of fiber-reinforced composite has a plurality of longitudinally extending fibers disposed in a resin matrix material and formed in the shape of a rod and the outer sheath has woven or braided fibers impregnated with a resin matrix material in the form of a sleeve.

In a method of manufacturing the formable fiber-reinforced composite material herein a rod is provided or fabricated of longitudinally extending fibers disposed in a resin matrix material. The resin matrix material is cured to provide a solid rod. A sheath of woven fibers is placed around the rod. The rod with the sheath thereon is treated to remove the resin matrix material. Treatment may be in the form of heat or chemical solution. If a chemical solvent is used, the fibers may be additionally heated.

The resulting material contains a rod of longitudinally extending fibers enveloped by a sheath of braided or woven fibers. Thereafter, the rod and sheath are impregnated with a resin matrix material. The resin is left uncured or partially cured to provide a formable fiber-reinforced composite material. The formable material may be furthered flattened to provide flattened strips of material or may be left in the shape of circular rods of material.

DESCRIPTION OF THE INVENTION

Figure 1:
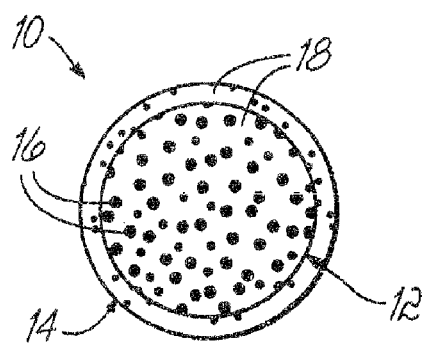
FIG. 1 shows the formable fiber-reinforced composite of the invention.

As will be appreciated, the present invention provides a fiber-reinforced composite having a rod of longitudinally extending fibers disposed in a composite and a sheath of woven or braided fibers enveloping the rod. The fiber-reinforced composite is fabricated by forming a rod of longitudinally extending fibers impregnated in a resin. The sheath may be a sleeve of material that is applied around the rod such that it envelops the rod. The final product is a rod of longitudinally extending fibers disposed in, or impregnated with, a resin matrix material, which rod is surrounded by a sheath of woven or braided fibers impregnated with a resin matrix material. The sheath and rod are held together by the resin matrix material.

Fibers in the fiber-reinforced composite and in the sheath may include glass, ceramic, metal, carbon, graphite, polymeric such as cellulose, polyamide, aramid, polyester, polyaramid, acrylic, vinyl and modacrylic, polyolefin, polytetrafluoroethylene, mixtures thereof, as well as other fibers known in the art. One preferred version of the rod is comprised of unidirectional microfilamentous glass fibers bundled in a resin matrix.

Resin materials may include those known in the art of dental materials, including, but not limited to, polyamides, polyester, polyolefins, polyimides, polyarylates, polyurethanes, vinyl esters or epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates (hereinafter abbreviated to PUDMA), and the like. Preferred polymeric matrix materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat. No. 5,276,068 to Waknine (which are herein incorporated by reference). An especially preferred methacrylate monomer is the condensation product of bisphenol A and glycidyl methacrylate, 2,2'-bis [4-(3-methacryloxy-2-hydroxy propoxy)-phenyl]-propane (hereinafter abbreviated "BIS-GMA").

The polymer matrix, which typically includes polymerization initiators, polymerization accelerators, ultra-violet light absorbers, anti-oxidants, fluorescent whitening agents, free radical initiators, and/or other additives well known in the art, may be visible light curable, self-curing, dual curing, or vacuum, heat, or pressure curable compositions, as well as any combination thereof. Heat and pressure or vacuum curable compositions include a heat cure initiator such as benzoyl peroxide, 1,1'-azobis(cyclohexanecarbo-nitrile) or other free radical initiators. The preferred polymeric matrix is a light and heat curable matrix, wherein light effects partial cure of the polymer matrix, while final curing is by heat under controlled atmosphere.

Examples of fiber reinforced composite materials comprising the reinforcing component in a polymeric matrix material are disclosed in U.S. Pat. Nos. 4,717,341 and 4,894,012 to Goldberg et al., U.S. Pat. No. 6,039,569 to Prasad et al., U.S. Pat. No. 6,030,220 to Karmaker et al, U.S. Pat. No. 5,564,929 to Alpert, and U.S. Pat. No. 5,919,044 to Sicurelli, Jr. et al., all of which are hereby incorporated by reference.

The resin matrix in the rod prior to heat treatment and that used in the rod and sheath after heat treatment may be a thermoplastic or thermoset resin.

In order to enhance the bond between the fibers and polymeric matrix, thereby enhancing the reinforcing effect, the fibers may be silanized or otherwise treated such as by grafting functional monomers or by surface modification by corona, high voltage flame or plasma treatment, to obtain proper coupling between the fibers and the resin matrix. Silanization renders the fibers hydrophobic, reducing the water sorption and improving the hydrolytic stability of the composite material, renders the fibers organophilic, improving wetting and mixing, and bonds the fibers to the polymeric matrix. Typical silane is A-174 (p-methacrylate propyl trimethoxy silane), produced by OSI Specialties, New York.

Fillers having an aspect ratio $\geq 1.0$ may be present in addition to or instead of fibers in an amount up to about 80 wt %, and preferably about 70 wt %. If fibers are present, the amount of filler is less than about 30 wt % of one or more fillers known in the art and used in dental restorative materials. Suitable fillers include those capable of being covalently bonded to the polymeric matrix itself or to a coupling agent that is covalently bonded to both. Fillers include silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide, and titania, among other conventional fillers such as those disclosed in commonly assigned U.S. Pat. Nos. 4,544,359 and 4,547,531 to Waknine (which are incorporated herein by reference), while possible coupling agents include silanes, zirconates, and titanates.

The rod is fabricated of continuous fibers impregnated into a resin and the rod is cured to produce a fiber-reinforced composite rod having fibers disposed in a resin matrix. Fibers are braided or woven to form a sheath and the sheath is applied to the cured rod to surround it. The sheath may be in the form of a long sleeve that can be slipped over the rod. The rod and the sheath surrounding it are heat treated to burn off the resin and release the memory of the woven or braided fibers contained in the sheath. If the sheath is made of organic fibers, the melting point of the resin matrix of the rod should be much lower than that of the fibers used to make the sheath so that the resin matrix in the rod can be burned off without melting or distorting the fibers in the sheath.

The heat treatment step is in the range of from about 100 to about 1200° C., preferably from about 150 to about 800° C., and most preferably from about 200 to about 500° C.

The resin matrix of the rod can also be dissolved chemically. In this case, the rod matrix materials and the sheath fibers cannot be dissolved in the same solvent. For example, the matrix of the rod can be fabricated of a water-soluble polymer such as polyvinyl alcohol (PVA) or an acetone-soluble polymer such as polyvinyl acetate (PVAC), water, acetone, alcohol, xylene, acids or mixtures thereof. As an another option, they may be additionally heated thereafter.

The resultant fiber bundle will have long fibers in the core and woven/braided fibers in the skin (sheath). The fiber bundle and sheath are subsequently resin-coated to provide a fiber-reinforced composite material having an inner core of longitudinally extending fibers dispersed in a resin and an outer sheath surrounding the inner core whereby the outer sheath contains woven fibers impregnated with a resin. The matrix resin can be further filled with particulate fillers and short fibers to provide additional reinforcement.

The composite material may be left uncured or may be partially cured. It may remain unflattened to provide a circular cross-section or may be further flattened under appropriate mechanical pressure to compact the core and sheath fibers. The cross-section of the (core and sheath) composite can also be circular. In this case the impregnated fibers will be passed through appropriate dies to compact the core and sheath fibers. While compacting, the resin coated fiber bundle can also be partially prepolymerized to increase the viscosity and thus improve formability.

Fibers may be present in the core material in an amount from about 10 to about 90% by weight of the resin matrix material and preferably about 20 to about 85% of the resin matrix material, and more preferably about 30 to about 80% of the resin matrix material. Fibers may be present in the sheath material in an amount from about 10 to about 90% by weight of the resin matrix material and preferably about 20 to about 85% of the resin matrix material, and more preferably about 30 to about 80% of the resin matrix material.

The prepared composite will not fray upon cutting or forming. While the core is made of continuous fibers, the strength of the composite will be higher. Consequently, composite is made with high strength and better formability.

Figure 2:
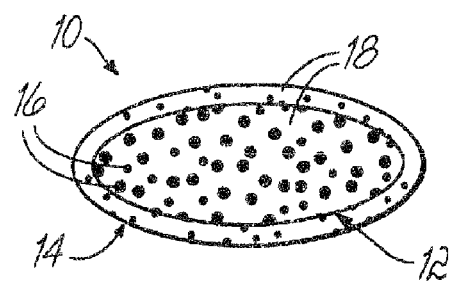
FIG. 2 shows an alternate embodiment of the fiber-reinforced composite.
Figure 3:
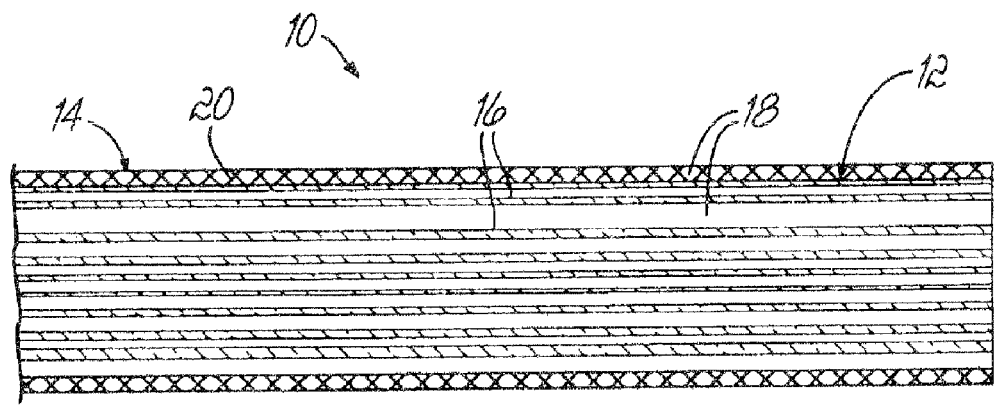
FIG. 3 shows a cross-sectional view of a side elevational view of the formable fiber-reinforced composite of the invention.

FIG. 1 shows a formable fiber-reinforced composite material 10 made in accordance herein showing the inner core section 12 surrounded by sheath 14. Core 12 has longitudinally extending fibers 16 disposed in a resin matrix 18. FIG. 2 shows a flattened version of the material 10 in FIG. 1. FIG. 3 shows a side elevational view of the material 10 in FIG. 1. Sheath 14 has fibers 20 in woven form impregnated with resin matrix 18. The flexural strength (MOR) of the cured fiber-reinforced composite material described herein is in the range from about 100 to 800 MPa and the modulus is in the range from about 5 to about 35 GPa.

The following non-limiting examples illustrate the invention.

EXAMPLES

Three separate sets of samples were fabricated. The first set of samples contained a sheath fabricated of braided glass fibers. The second set of samples sample contained a composite rod having a diameter of 0.60 mm and fabricated from glass fiber and vinyl ester. A glass fiber sheath of about 0.05 mm thickness was then braided around the rod. The final diameter of the rod with the braided sheath applied thereto was about 0.70 mm. The third set of samples contained commercially available Splint-It® material available from Pentron Clinical Technologies, LLC, Wallingford, Conn. The samples were cut into small pieces of about 6 inches in length and heat treated as follows: Temperature 1=100° C. for 30 minutes; Temperature 2=150° C. for 30 minutes; and Temperature 3=500° C. for 4 hours The heat treatment burned off the resin, leaving the unidirectional fibers in the core surrounded by braided fibers outside as a sheath. The burning of cured resin inside the rod also created space for new uncured resin to penetrate. In both cases the fraying of fibers was very minimal or none due to the heat treatment. The treatment temperature and time can further be optimized to minimize the fraying by controlling the memory of fibers.

All the samples were then silane treated and air dried. The dry fibers were impregnated with a dental resin mixture of Bis-GMA, hexanediol dimethacrylate ("HDDMA") and 1,6-Bis(methacrylethyloxycarbonylamino) trimethyloxane ("UDMA") containing heat and light cure initiators. The impregnated fibers were packed into a metal mold with a cavity size of 1×2×25 mm or 2×2×25 mm. The samples were cured as follows: light cured for 2 minutes inside the mold and light cured for 2 minutes outside the mold, using the Cure-Lite plus curing light (Pentron) and heat and vacuum cured for 15 minutes using the Conquest curing unit (Pentron).

Three point-bend testing was conducted using the Universal Testing Machine (H5KS, Tinius Olsen) at a test speed of 0.51 mm/min. The results (average of 3 specimens) are given in Table 1 below:

The normalized (on 100% fiber) flexural strengths were about 800 and 1046 MPa respectively for sheath only and sheath and core groups calculated by dividing the strength value with the fiber fraction.

As will be appreciated, the present invention provides a fiber-reinforced composite material having good strength and formability properties. Dental materials formed herein are useful in the formation of dental restorative materials, including, but not limited to, crowns, partial crowns, bridges, frameworks, clasps, inlays, onlays, facings, fillings, splints, partial and full dentures, veneers, facets, cylinders, abutments, connectors, teeth, tooth replacement appliances, implants, posts, cores, space maintainers, jackets and orthodontic materials.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

The invention claimed is:

1. A formable fiber-reinforced composite comprising:
    an inner core and an outer sheath;
    wherein the inner core comprises longitudinally extending fibers and the outer sheath comprises braided or woven fibers;
    wherein the fibers have been treated to release the elastic memory thereof; and
    wherein the fibers are impregnated with a resin matrix material.

2. The formable fiber-reinforced composite of claim 1 wherein the inner core is in the shape of a rod.

3. The formable fiber-reinforced composite of claim 2 wherein the rod and sheath thereon is flattened.

4. The formable fiber-reinforced composite of claim 2 wherein the resin matrix material in the fiber-reinforced composite is partially cured.

TABLE 1

| Fiber type | Thickness (mm) | Width (mm) | Breaking Load (N) | MOR (MPa) | Modulus (GPa) | Fiber content (Weight %) |
|---|---|---|---|---|---|---|
| Sheath Only | 1.0 | 2.0 | 34.1 | 490.2 | 21.5 | 61.3 |
| Sheath + Core | 1.2 | 2.0 | 73.7 | 696.8 | 27.1 | 66.6 |
| Commercially available Splint-It ®* | 1.1 | 2.1 | 13.6 | 169 | 9.0 | 50.0 |
| Commercially available Splint-It ®* | 2.2 | 2.2 | 79.5 | 220 | 9.2 | 50.0 |

*Pentron Clinical Technologies, LLC Wallingford, CT

Having unidirectional fibers in the core increased both the flexural strength (MOR) and modulus. Both the sheath and the core and sheath samples show higher flexural strength and modulus than Splint-It® material.

5. The formable fiber-reinforced composite of claim 2 wherein the resin matrix material in the fiber-reinforced composite is uncured.

6. The formable fiber-reinforced composite of claim 1 wherein the resin matrix material comprises acrylics, methacrylics, polyamides, polyester, polyolefins, polyimides, polyarylates, polyurethanes, vinyl esters or epoxy-based materials, styrenes, styrene acrylonitriles, ABS polymers, polysulfones, polyacetals, polycarbonates, polyphenylene sulfides, polyarylsulfides, acrylonitrile butadiene-styrene copolymers, polyurethane dimethacrylates ("PUDMA"), the condensation product of bisphenol A and glycidyl methacrylate, 2,2-bis[4-(3-methacryloxy-2-hydroxy propoxy)-phenyl]-propane ("BIS-GMA"), hexanediol dimethacrylate ("HDDMA"), 1,6-bis(methacrylethyloxy carbonylamino) trimethyloxane ("UDMA") or a mixture thereof.

7. The formable fiber-reinforced composite of claim 1 wherein the longitudinally extending fibers and the braided or woven fibers comprise the same material.

8. The formable fiber-reinforced composite of claim 1 wherein the longitudinally extending fibers comprise glass, ceramic, metal, carbon, graphite, polymeric, cellulose, polyamide, aramid, polyester, polyaramid, acrylic, vinyl, modacrylic, polyolefin, polytetrafluoroethylene or mixtures thereof.

9. The formable fiber-reinforced composite of claim 1 wherein the braided or woven fibers comprise glass, ceramic, metal, carbon, graphite, polymeric, cellulose, polyamide, aramid, polyester, polyaramid, acrylic, vinyl, modacrylic, polyolefin, polytetrafluoroethylene or mixtures thereof.

10. The formable fiber-reinforced composite of claim 1 for use as crowns, partial crowns, bridges, frameworks, clasps, inlays, onlays, facings, fillings, splints, partial and full dentures, veneers, facets, cylinders, abutments, connectors, teeth, tooth replacement appliances, implants, posts, cores, space maintainers, jackets and orthodontic materials.

11. The formable fiber-rein forced composite of claim 1 wherein the fibers in the core are present in the range of 10 to about 90% of the resin matrix material.

12. The formable fiber-reinforced composite of claim 1 wherein the fibers in the sheath are present in the range of 10 to about 90% of the resin matrix material.

13. The formable fiber-reinforced composite of claim 1 wherein the fiber-reinforced composite, after curing, exhibits a flexural strength (MOR) equal to or greater than about 100 MPa and a modulus of elasticity equal to or greater than about 5 GPa.

14. The formable fiber-reinforced composite of claim 1 wherein the formable fiber-reinforced composite is in the form of strips of material.

15. The formable fiber-reinforced composite of claim 1 wherein the resin matrix material comprises a filler material.

16. A method of making a formable fiber-reinforced composite material for use as a dental restorative material comprising:
  providing a rod fabricated of longitudinally extending fibers disposed in a first resin matrix material;
  applying a sheath around the rod, wherein the sheath comprises woven or braided fibers;
  treating the rod with sheath thereon to remove the first resin matrix material and release the memory of the fibers;
  impregnating the rod with sheath with a second resin matrix material to provide a formable fiber-reinforced composite material.

17. The method of claim 16 wherein the first and second resin matrix material comprise the same material.

18. The method of claim 16 wherein the first and second resin matrix material comprise different materials.

19. The method of claim 16 wherein the first resin matrix material is either a thermoplastic or thermoset material.

20. The method of claim 16 wherein the second resin matrix material is either a thermoplastic or thermoset material.

21. The method of claim 16 wherein the first and second resin matrix materials comprises acrylics, methacrylics, polyamides, polyester, polyolefins, polyimides, polyarylates, polyurethanes, vinyl esters or epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates ("PUDMA"), the condensation product of bisphenol A and glycidyl methacrylate, 1,1'-bis[4-(3-methacryloxy-2-hydroxy propoxy)-phenyl]-propane ("BIS-GMA"), hexanediol dimethacrylate ("HDDMA"), 1,6-bis(methacrylethyloxy carbonylamino) trimethyloxane ("UDMA") or a mixture thereof.

22. The method of claim 16 wherein the longitudinally extending fibers comprise glass, ceramic, metal, carbon, graphite, polymeric, cellulose, polyamide, aramid, polyester, polyaramid, acrylic, vinyl, modacrylic, polyolefin, polytetrafluoroethylene or mixtures thereof.

23. The method of claim 16 wherein the braided or woven fibers comprise glass, ceramic, metal, carbon, graphite, polymeric, cellulose, polyamide, aramid, polyester, polyaramid, acrylic, vinyl, modacrylic, polyolefin, polytetrafluoroethylene or mixtures thereof.

24. The method of claim 16 wherein the second resin matrix material is uncured.

25. The method of claim 16 wherein the second resin matrix material is partially cured.

26. The method of claim 16 further comprising flattening the impregnated rod with sheath to provide a flattened formable fiber-reinforced composite material.

27. The method of claim 16 wherein the step of treating the rod with sheath comprises heating the rod with sheath in a range from about 100° C. to about 1200° C. to remove the first resin matrix material.

28. The method of claim 16 wherein the step of treating the rod with sheath comprises treating the rod with sheath with a chemical solution to dissolve the first resin matrix material.

29. The method of claim 28 wherein the chemical solution comprises water, acetone, alcohol, xylene, acids or mixtures thereof.

30. The method of claim 16 wherein the second resin matrix comprises polymerization initiators, polymerization accelerators, ultra-violet light absorbers, anti-oxidants, fluorescent whitening agents, free radical initiators, or mixtures thereof.

31. The method of claim 16 wherein the resin matrix comprises visible light curable, self-curing, dual curing, vacuum, heat, or pressure curable initiators, accelerators or mixtures thereof.

32. The method of claim 31 wherein the heat curable initiator comprises benzoyl peroxide or 1,1'-azobis(cyclohexanecarbo-nitrile).

33. The formable fiber-reinforced composite of claim 1 wherein the resin matrix material comprises acrylics, methacrylics, polyamides, polyester, polyolefins, polyimides, polyarylates, polyurethanes, vinyl esters or epoxy-based materials, styrenes, styrene acrylonitriles, ABS polymers, polyacetals, polycarbonates, polyphenylene sulfides, polyarylsulfides, acrylonitrile-butadiene-styrene copolymers, polyurethane dimethacrylates ("PUDMA"), the condensation product of bisphenol A and glycidyl methacrylate, 2,2'-bis[4-(3-methacryloxy-2-hydroxy propoxy)-phenyl]-propane ("BIS-GMA"), hexanediol dimethacrylate ("HDDMA"), 1,6-bis(methacrylethyloxy carbonylamino) trimethyloxane ("UDMA") or a mixture thereof.

34. The formable fiber-reinforced composite of claim 1 wherein the longitudinally extending fibers comprise glass, ceramic, metal, graphite, polymeric, cellulose, polyamide, aramid polyester, polyaramid, acrylic, vinyl, modacrylic, polyolefin, polytetrafluoroethylene or mixtures thereof.

* * * * *

UNITED STATES PATENT AND TRADEMARK OFFICE
CERTIFICATE OF CORRECTION

PATENT NO. : 7,673,550 B2
APPLICATION NO. : 11/385595
DATED : March 9, 2010
INVENTOR(S) : Ajit Karmaker and Arun Prasad It is certified that error appears in the above-identified patent and that said Letters Patent is hereby corrected as shown below:

Col. 2, line 29, "may be furthered flattened" should read --may be further flattened--.

Col. 5, line 11, "set of samples sample contained" should read --set of samples contained--.

Col. 7, line 32, Claim 11, "fiber-rein forced composite" should read --fiber-reinforced composite--.

Col. 8, line 5, Claim 21, "matrix materials comprises" should read --matrix materials comprise--.

Col. 8, line 12, Claim 21, "1,1'-bis" should read --2,2'-bis--.

Col. 10, line 4, Claim 34, "aramid polyester" should read --aramid, polyester--.

Signed and Sealed this

Twenty-ninth Day of June, 2010

David J. Kappos
*Director of the United States Patent and Trademark Office*